US009861651B2

(12) United States Patent
Brown et al.

(10) Patent No.: US 9,861,651 B2
(45) Date of Patent: Jan. 9, 2018

(54) USE OF NICOTINAMIDE RIBOSIDE TO TREAT HEARING LOSS

(71) Applicant: Cornell University, Ithaca, NY (US)

(72) Inventors: Kevin Brown, New York, NY (US); Anthony Sauve, New Rochelle, NY (US); Samie Jaffrey, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 22 days.

(21) Appl. No.: 14/414,924

(22) PCT Filed: Jul. 15, 2013

(86) PCT No.: PCT/US2013/050511
§ 371 (c)(1),
(2) Date: Jan. 15, 2015

(87) PCT Pub. No.: WO2014/014828
PCT Pub. Date: Jan. 23, 2014

(65) Prior Publication Data
US 2015/0174148 A1 Jun. 25, 2015

Related U.S. Application Data

(60) Provisional application No. 61/672,169, filed on Jul. 16, 2012.

(51) Int. Cl.
A61K 31/706 (2006.01)
G01N 33/50 (2006.01)

(52) U.S. Cl.
CPC ....... A61K 31/706 (2013.01); G01N 33/5058 (2013.01); G01N 2500/10 (2013.01)

(58) Field of Classification Search
CPC .................................................. A61K 31/706
See application file for complete search history.

(56) References Cited

U.S. PATENT DOCUMENTS

2007/0149466 A1* 6/2007 Milburn ................ A61K 31/00
514/43
2009/0306225 A1* 12/2009 Lichter ................ A61K 9/0046
514/772.1

FOREIGN PATENT DOCUMENTS

| JP | 2006-510047 A | 3/2009 |
| WO | WO 2007/008548 A2 | 1/2007 |
| WO | WO 2007/119098 A2 | 10/2007 |

OTHER PUBLICATIONS

Definition of prevent, Oxford English Dictionary Online, http://dictionary.oed.com/, accessed online Mar. 27, 2010, especially definition 9a. at p. 2.*

WebMD entry for hearing loss prevention, WebMD website, http://www.webmd.com/atozguides/hearinglossprevention, accessed online on Sep. 15, 2016.*
Verdin et al., Trends Biochem. Sci., 2010, 35(12), p. 669-675.*
Araki et al., "Increased Nuclear NAD Biosynthesis and SIRT1 Activation Prevent Axonal Degeneration", Science, 305: 1010-1013 (2004).
Avery et al., "WldS Prevents Axon Degeneration through Increased Mitochondrial Flux and Enhanced Mitochondrial Ca2+ Buffering", Current Biology, 22: 596-600 (2012).
Coleman et al., "An 85-kb tandem triplication in the slow Wallerian degeneration (Wlds) mouse", Proc. Natl. Acad. Sci. USA, 95: 9985-9990 (1998).
Gilley et al., Endogenous Nmnat2 Is an Essential Survival Factor for Maintenance of Healthy Axons, PLoS Biology, 8(1): 1-18 (2010).
Kaneko et al., "Protecting Axonal Degeneration by Increasing Nicotinamide Adenine Dinuclcotide Levels in Experimental Autoimmune Encephalomyelitis Models", Journal of Neuroscience, 26(38): 9794-9804 (2006).
Kujawa et al., "Adding Insult to Injury: Cochlear Nerve Degeneration after "Temporary" Noise-Induced Hearing Loss", Journal of Neuroscience, 29(45): 14077-14085 (2009).
Lin et al., "Primary Neural Degeneration in the Guinea Pig Cochlea After Reversible Noise-Induced Threshold Shift", Journal of the Association for Research in Otolaryngology, 12: 605-616 (2011).
Press et al., "Nmnat Delays Axonal Degeneration Caused by Mitochondrial and Oxidative Stress", Journal of Neuroscience, 28(19): 4861-4871 (2008).
Puel et al., "Excitotoxicity and repair of cochlear synapses after noise-trauma induced hearing loss", Neuroreport, 9: 2109-2114 (1998).
Sajadi et al., "Wlds-Mediated Protection of Dopaminergic Fibers in an Animal Model of Parkinson Diseaseurrent Biology", Current Biology 14: 326-330 (2004).
Samsam et al.,"The Wlds Mutation Delays Robust Loss of Motor and Sensory Axons in a Genetic Model for Myclin-Related Axonopathy", Journal of Neuroscience, 23(7): 2833-2839 (2003).
Sasaki et al., "Nicotinamide Mononucleotide Adenylyl Transferase-Mediated Axonal Protection Requires Enzymatic Activity But Not Increased Levels of Neuronal Nicotinamide Adenine Dinucleotide", Journal of Neuroscience, 29(17): 5525-5535 (2009).
Spoendlin, "Retrograde Generation of the Cochlear Nerve", Acta Oto-Laryngologica, 79: 266-275 (1975).
Wang et al., "A local mechanism mediates NAD-dependent protection of axon degeneration", J. Cell Biol. 170(3): 349-355 (2005).
Wang et al., "Dynamics of Noise-Induced Cellular Injury and Repair in the Mouse Cochlea", Journal of the Association for Research in Otolaryngology, 3:248-268 (2002).

(Continued)

Primary Examiner — Jonathan S Lau
(74) Attorney, Agent, or Firm — Leydig, Voit & Mayer, Ltd.

(57) ABSTRACT

The invention provides a method of preventing or treating hearing loss in a mammal in need thereof. The method involves administering to the mammal an agent that increases intracellular NAD+ in the mammal. The invention also provides a method of determining if a compound acts as a neuroprotective agent.

9 Claims, 6 Drawing Sheets

(56) References Cited

OTHER PUBLICATIONS

Whitlon et al., "Cryoembedding and sectioning of cochleas for immunocytochemistry and in situ hybridization", *Brain Research Protocols*, 6: 159-166 (2001).
Willott, "Measurement of the Auditory Brainstem Response (ABR) to Study Auditory Sensitivity in Mice", *Current Protocols in Neuroscience*, 8.21B.1-8.21B.12 (2005).
Yang et al., "Syntheses of Nicotinamide Riboside and Derivatives: Effective Agents for Increasing Nicotinamide Adenine Dinucleotide Concentrations in Mammalian Cells", *J. Med. Chem.* 50: 6458-6461 (2007).
Harris et al., "Prevention of noise-induced hearing loss with Src-PTK inhibitors", *Hearing Research*, 208: 14-25, (2005).
Paddock, "Tiny Vitamin in Milk Makes for Mightier Mice", *Medical News Today*, 4 pages (2012).
Someya et al., "Sirt3 Mediates Reduction of Oxidative Damage and Prevention of Age-Related Hearing Loss under Caloric Restriction", *Cell*, 143(5): 802-812 (2010).
European Patent Office, Supplementary European Search Report in Application No. 13820653.7, dated Mar. 18, 2016, 6 pages.
PCT International Search Report in International Application No. PCT/US2013/050511, dated Nov. 27, 2013, 3 pages.
Canto et al., "The NAD Precursor Nicotinamide Riboside Enhances Oxidative Metabolism and Protects against High-Fat Diet-Induced Obesity", *Cell Metabolism*, 15: 838-847 (2012).
Fischel-Ghodsian et al., "Mitochondrial dysfunction in hearing loss", *Mitochondrian*, 4:675-694 (2004).

\* cited by examiner

USE OF NICOTINAMIDE RIBOSIDE TO TREAT HEARING LOSS

CROSS-REFERENCE TO RELATED APPLICATIONS

This application is the U.S. national phase of International Patent Application No. PCT/US2013/050511, filed Jul. 15, 2013, which claims the benefit of U.S. Provisional Patent Application No. 61/672,169, filed Jul. 16, 2012, the disclosures of which are incorporated herein by reference.

BACKGROUND OF THE INVENTION

Noise exposure is a major cause of hearing loss worldwide. Following noise exposure, damage to diverse structures in the cochlea are seen, including the spiral ganglia nerve fibers that normally form synaptic contacts with hair cells in the cochlea. These synapses enable the spiral ganglia to convey acoustic information from the cochlea to higher order structures in the brain stem. Following noise exposure, hair cells release neurotransmitters that lead to excitotoxic damage in the neurites, resulting in synaptic disruption and neurite retraction (Kujawa, S. G. et al., *J. Neuroscience*, 29, 14077-14085 (2009); Lin, H. W. et al., *Journal of the Association for Research in Otolaryngology*, 12, 605-616 (2011); Spoendlin, H., *Acta Oto-Laryngologica*, 79, 266-275 (1975)). Following moderate noise exposure and neurite refraction, some neurite regeneration can be seen, which restores synaptic connectivity and auditory capacity (Puel, J. L. et al., *Neuroreport*, 9, 2109-2114 (1998)). However, persistent noise exposure or intense acoustic trauma can result in permanent neurite degeneration.

Thus, there remains a need for new methods for preventing and/or treating noise-induced hearing loss.

BRIEF SUMMARY OF THE INVENTION

The invention provides a method of preventing or treating hearing loss in a mammal in need thereof. The method comprises administering to the mammal an effective amount of an agent that increases intracellular NAD+ in the mammal, thereby preventing or treating hearing loss in the mammal.

The invention also provides a method of determining if a compound acts as a neuroprotective agent. The method comprises (a) providing a mammal, (b) administering an agent to the mammal, (c) exposing the mammal to noise, and (d) determining the level of NAD+ in hearing-related cells of the mammal, thereby determining if the compound acts as a neuroprotective agent based on the level of NAD+ in hearing-related cells of the mammal.

BRIEF DESCRIPTION OF THE SEVERAL VIEWS OF THE DRAWING(S)

DETAILED DESCRIPTION OF THE INVENTION

Figure 1A:
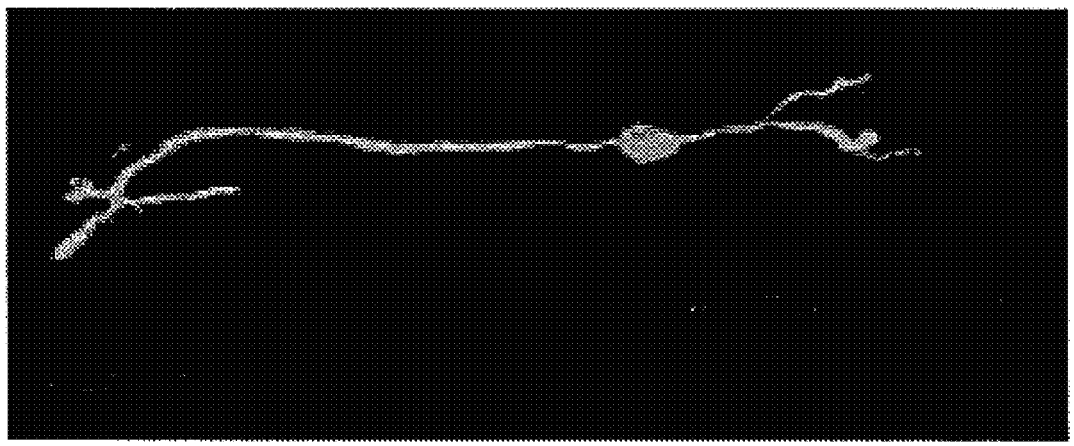
FIGS. 1A-1C depict representative NF-200 stains of untreated neurites (control), neurites treated with rotenone, and neurites treated with rotenone and NAD+, respectively.

The invention provides a method of preventing or treating hearing loss in a mammal in need thereof. The method comprises administering to the mammal an effective amount of an agent that increases intracellular NAD+ in the mammal, thereby preventing or treating hearing loss in the mammal.

The agent that increases intracellular NAD+ can be any suitable agent that increases intracellular NAD+. In an embodiment, the agent is nicotinamide riboside.

The hearing loss can be caused by a variety of circumstances. The hearing loss can be caused by noise exposure. The agent can be administered to the mammal before, during, and/or after noise exposure.

The hearing loss can be caused by drug toxicity. In certain embodiments, the drug toxicity results from treatment of the mammal with gentamicin or cisplatin. The agent can be administered before, during, and/or after exposure to the toxic drugs.

The hearing loss can be associated with Meniere's disease. Meniere's disease is a disorder of the inner ear that can affect hearing and balance to a varying degree. It is characterized by episodes of vertigo, low-pitched tinnitus, and hearing loss. The hearing loss associated with Meniere's disease has been suggested to involve excitotoxic damage to spiral ganglia neurons.

Other causes of hearing loss may also be successfully treated by this agent including age-associated hearing loss, sudden idiopathic hearing loss, otitis media in all its forms, and barotrauma to the ear.

Hearing implants such as cochlear implants endeavor to preserve native hearing while placing a implantable device in the ear. This hearing preservation may be accentuated by applications of the agent increases intracellular NAD+.

Comorbid conditions with hearing loss including vertigo (dizziness), tinnitus (ringing in ear) and hyperacusis (sensitivity to loud noises) may also be effectively treated by the agent increases intracellular NAD+.

In any of the above embodiments, the agent increases intracellular NAD+ in one or more cells selected from the group consisting of spiral ganglia nerve cells, hair cells, supporting cells, and Schwann cells. In certain embodiments, the agent suppresses oxidative damage in the cell. In certain embodiments, the agent activates SIRT3. Endogenous SIRT3 is a soluble protein located in the mitochondrial matrix. Overexpression of SIRT3 in cultured cells increases respiration and decreases the production of reactive oxygen species. Without wishing to be bound by any particular theory, it is believed that activation of SIRT3 is implicated in suppression of oxidative damage in the aforesaid cells.

In certain embodiments, the treating of the mammal with the agent results in prevention of hearing loss. In other embodiments, the treating of the mammal with the agent results in the mitigation of hearing loss.

The agent that increases intracellular NAD+ can be administered using any suitable method. For example, the agent that increases intracellular NAD+ can be administered orally, by injection, or by intratympanic injection into the middle ear space.

As used herein, the term "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. For example, an effective amount of the agent that increases intracellular NAD+ can be an amount effective to inhibit, attenuate, or reverse hearing loss symptoms. The specific effective amount may vary with such factors as the particular condition being treated, the physical condition of the patient, the type of mammal being treated, the duration of the treatment, the nature of concurrent therapy (if any), the specific formulations employed, and the structure of the agent.

The doses of the agent administered to a mammal, particularly, a human, in accordance with the invention should be sufficient to effect the desired response. Such responses include reversal or prevention, in whole or in part, of the hearing loss. One skilled in the art will recognize that the agent dosage and administration regimen will depend upon a variety of factors, including the age, condition, and body weight of the mammal, as well as the particular type of the cause of hearing loss and extent of the hearing loss in the mammal. The size of the doses will also be determined by the routes, timing, and frequency of administration as well as the existence, nature, and extent of any adverse side-effects that might accompany the administration of the agent that increases intracellular NAD+ and the desired physiological effect. The treatment of hearing loss may require prolonged treatment involving multiple administrations of the agent to the mammal.

Suitable agent doses and administration regimens can be determined by conventional range-finding techniques known to those of ordinary skill in the art. Generally, treatment is initiated with smaller dosages that are less than the optimum dose of the agent that increases intracellular NAD+. Thereafter, the dosage is increased by small increments until the optimum effect under the circumstances is reached. The inventive method typically will involve the administration of about 0.1 to about 300 mg of the agent that increases intracellular NAD+ described above per kg body weight of the mammal.

The agent that increases intracellular NAD+ can be administered to the mammal by itself or in the form of a pharmaceutical composition comprising the agent and a pharmaceutically acceptable carrier.

The agent that increases intracellular NAD+ can be administered in a pharmaceutical composition, i.e., in admixture with one or more suitable pharmaceutical diluents, extenders, excipients, or carriers (collectively referred to herein as a pharmaceutically acceptable carrier) suitably selected with respect to the intended form of administration and as consistent with conventional pharmaceutical practices. The pharmaceutical composition can be in any suitable form, for example, in a form suitable for oral, direct injection, or intratympanic administration. The carrier can be a solid or liquid, and the type of carrier is generally chosen based on the contemplated route of administration.

The agent that increases intracellular NAD+ can be co-administered along with the pharmaceutically acceptable carrier in the form of a tablet or capsule, liposome, as an agglomerated powder, or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include (a) solutions or suspensions in water, pharmaceutically acceptable fats and oils, alcohols or other organic solvents (including esters), (b) emulsions, (c) syrups, (d) elixirs, (e) tinctures, suspensions, (f) suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the comtemplated route of administration, for example, by bolus or infusion. Injectable forms may include, for example, intraperitoneal, subcutaneous, or intramuscular forms. In some embodiments, the agent that increases intracellular NAD+ can be administered in the form of a nutraceutical, that is, in admixture with foodstuffs or beverages. In some embodiments, the pharmaceutical composition may include the agent that increases intracellular NAD+ may include other compounds also used to treat neurite damage.

The invention also provides a method of determining if a compound acts as a hearing protective agent. The method comprises (a) providing a mammal, (b) administering an agent to the mammal, (c) exposing the mammal to noise, and (d) determining the level of NAD+ in hearing-related cells of the mammal, thereby determining if the compound acts as a hearing protective agent based on the level of NAD+ in hearing-related cells of the mammal.

It can be difficult to know if a compound will be useful as a hearing protective agent. As described herein, it has been found that hearing loss is a sirtuin and NAD+-sensitive pathway and that nicotinamide riboside protects against and treats hearing loss, especially noise-induced hearing loss. Thus, a determination can be made as to whether a compound can prevent and/or treat hearing loss by evaluating whether the compound acts in neurons by using noise-induced hearing loss paradigms. If the compound is able to increase NAD+ in hearing-related cells, then that compounds will exhibit protection from, and be able to treat hearing loss, especially noise-induced hearing loss.

EXAMPLES

The following examples further illustrate the invention but, of course, should not be construed as in any way limiting its scope.

The following abbreviations are used herein: HBSS−/−, Hanks Balanced Salt Solution; DMEM, Dulbecco's Modified Eagle Medium; PBS, phosphate buffered saline; BSA, bovine serum albumin; DAPI, 4',6-diamidino-2-phenylindole.

Nicotinamide riboside was synthesized as previously described in Yang, T. et al., *J. Med. Chem.* 50, 6458-6461 (2007). Other chemicals and reagents were purchased from Sigma except as otherwise indicated below.

Male and female C57/BL6J mice were purchased from Jackson Laboratories. WldS$^{+/+}$ mice were a kind gift of Dr. Michael Coleman (Babraham Institute, University of Cambridge).

Spiral Ganglia Neuron Culture

Dissociated spiral ganglia neurons were harvested from P5 rats. Briefly, pups were rapidly decapitated, and cochlea were dissected. The modiolus was then dissected and digested (0.1% trypsin, 0.1% collagenase, HBSS−/−) for 45 min at 37° C. Sequential trituration was performed with fire-polished pipets to release cells from the tissue, and cells were transferred to laminin/polylysine-coated 24-well plates. Neurons were incubated overnight in culture media (DMEM high glucose, N2 supplement, 10 μg/ml insulin, 25 μg/ml BDNF, 25 μg/ml NT3). To elicit neurite degeneration, cultures were incubated with rotenone (10 μM) for 2 hr in the presence/absence of 10 mM NAD+.

Cellular Immunohistology

Spiral ganglia neuron cultures were fixed with 4% paraformaldehyde and permeabilized with 0.5% Triton X-100™/PBS for 10 min. After washing, cells were blocked with 4% donkey serum and incubated with mouse anti-NF200 (1:1000) overnight at 4° C. Neurite beading was then measured using a previously described, unbiased computerized protocol (Sasaki, Y. et al., *J. Neuroscience*, 29, 5525-5535 (2009)).

Cochlear Histology/Immunohistology

Mouse cochlea were prepared as described in Whitlon, D. S. et al., *Brain Research Protocols*, 6, 159-166 (2001). Mouse cochlea were quickly dissected from the temporal bone following rapid decapitation. Once separated, the apex of the cochlea was gently fenestrated, and the cochlea were immediately fixed in 4% paraformaldehyde overnight at 4° C. The cochlea were then washed with three changes of PBS and incubated in a decalcification solution (10% EDTA/PBS pH 7.4) under constant rotation at 4° C. for 1 week. The decalcification solution was changed daily. Cochlea were washed in 3 changes of PBS and then treated with progressively increasing sucrose concentrations from 10-30%. The cochlea were incubated overnight in 30% sucrose at 4° C. The cochlea were incubated an additional 24 hr in OCT compound (Tissue-Tek). Following the final incubation, the cochlea were transferred to cryomolds, carefully aligning the modiolus parallel to the bottom of the mold, and frozen over dry ice. Mid-modiolar samples were then cut at a 10 μm thickness and mounted on glass slides (VWR SUPER-FROST™ Plus). Sections were then dried for 2 hr prior to staining.

Slides were then post-fixed with 1.5% paraformaldehyde for 5 min. Slides were washed and then incubated with 0.5% Triton X-100/PBS for 15 min. The slides were again washed and then blocked with 2% BSA/PBS. Sections were then incubated with ALEXA FLUOR™ 488 (phalloidin-488) (Invitrogen) as per the manufacturer's instructions for 20 min. The slides were then washed and then incubated with 1:1000 rabbit anti-heavy neurofilament antibody overnight at 4° C. The slides were then washed and incubated with 1:1000 ALEXA FLUOR™ 546 goat anti-rabbit antibody (Invitrogen) for 1 hr at room temperature. After a final wash, sections were mounted with ProLong™ Gold antifade reagent with DAPI (Life Technologies). Three-color epifluorescence imaging was performed using a Nikon Eclipse Ti microscope with a Coolsnap HQ2 camera.

Auditory Testing

Auditory brainstem response testing was performed as previously described (Willott, J. F., *Current Protocols in Neuroscience*, 8.21B, B1-B12 (2005). Animals were tested following sedation with ketamine and xylazine (40 mg/kg and 10 mg/kg, respectively). Tone burst stimuli at 8, 16, and 32 kHz for 0.5 msec were used to elicit auditory evoked responses using an auditory brainstem recording system (Intelligent Hearing Systems, Miami, Fla.). An evoked response was determined by identifying waveforms at proper time intervals that increased in magnitude with increasing volume as described previously by Willott.

Noise Exposure

Animals were exposed to a 90 dB octave band for 2 hr in a cage placed in a soundproof chamber (MAC-2, Industrial Acoustics Company, Bronx N.Y.). The mice were able to freely move throughout the cage. The octave band was generated using ToneGen software (NCH software, Greenwood Village, Colo.) routed through an Audiosource Amp100 amplifier driving two down-facing Fostex FT-96H speakers. The sound pressure level was confirmed at 0, 30, 60, and 90 min, and again just prior to completion of sound exposure using an Extech microphone 407736.

Example 1

This example demonstrates that spiral ganglia neuritis possess the NAD-regulated signaling pathway that has previously been shown to prevent axonal degeneration.

Figure 1B:
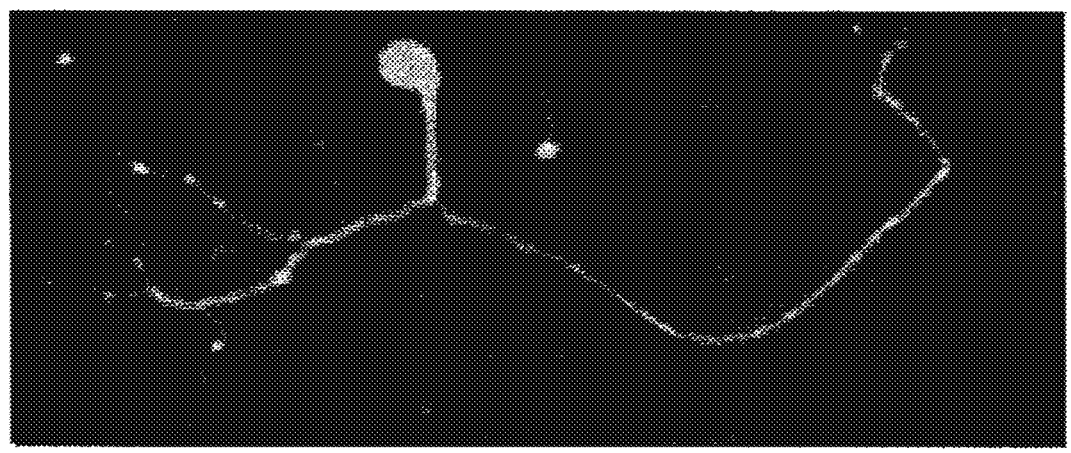
Figure 1C:
Figure 2:
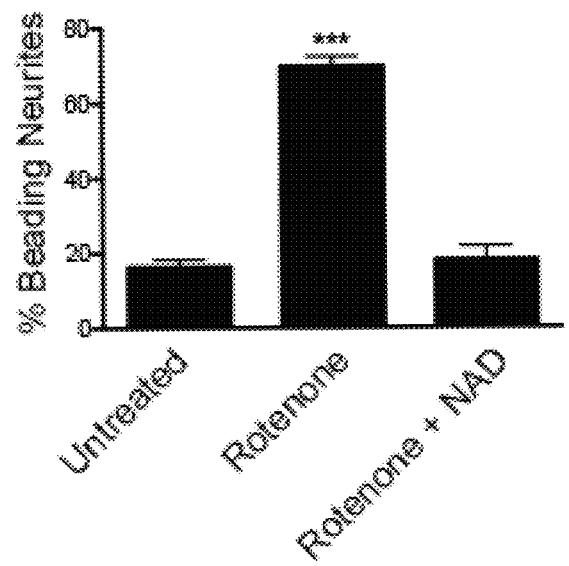
FIG. 2 is a graphical representation of the percentage of beading neurites in untreated neurites (control), neurites treated with rotenone, and neurites treated with rotenone and NAD+.

Axonal degeneration in a variety of neurons can be blocked by treatment with millimolar concentrations of NAD+ (Avery, M. A., et al., *Current Biology*, CB 22, 596-600 (2012)). To determine if spiral ganglia neurites also possessed this NAD-sensitive pathway, axonal degeneration was elicited using rotenone, which is a mitochondrial complex I inhibitor that has previously been shown to induce axonal degeneration in axons of dorsal root ganglia neurons (Press, C. et al., *J. Neuroscience*, 28, 4861-4871 (2008)). Treatment of P5 DIV3 rat spiral ganglia neurons with 10 μM rotenone resulted in neurite degeneration in as early as 2 hr, as measured by the presence of neurite blebbing. This effect was blocked by simultaneous treatment of neurons with 10 mM NAD+. Representative NF-200 stains of untreated neurites (control), neurites treated with rotenone, and neurites treated with rotenone and NAD+ are depicted in FIGS. 1A-1C, respectively. The percentage of beading neurites in untreated neurites (control), neurites treated with rotenone, and neurites treated with rotenone and NAD+ are illustrated graphically in FIG. 2. These data indicate that spiral ganglia neurites possess the NAD+-regulated signaling pathway that has previously been shown to prevent axonal degeneration.

Example 2

This example demonstrates that genetic enhancement of endogenous NAD+ biosynthetic pathways reduces noise-induced hearing loss. The Wallerian degeneration slow (WldS) mouse expresses a triplicate repeat of a gene fusion of the NAD biosynthetic enzyme Nicotinamide mononucleotide adenylyl transferase 1 and Ube4a (Coleman, M. P, et al., *Proc. Natl. Acad. Sci. USA*, 95, 9985-9990 (1998)). WldS is highly expressed in neurons, and its expression markedly delays degeneration of the distal axonal fragment following axonal transaction (Araki, T. et al., *Science*, 305, 1010-1013 (2004)). WldS expression also mitigates disease phenotypes of mice that are susceptible to various neurodegenerative diseases (Samsam, M., et al., *J. Neuroscience*, 23, 2833-2839 (2003); Kaneko, S. et al., *J. Neuroscience*, 26, 9794-9804 (2006); Sajadi, A. et al., *Current Biology*, CB 14, 326-330 (2004)). WldS acts in axons to maintain axonal NAD biosynthesis after axonal injuries (Wang, J, et al., *J.*

*Cell Biol.* 170, 349-355 (2005)), which typically results in the loss of endogenous NAD biosynthetic enzymes (Gilley, J. et al., *PLoS Biology,* 8, e1000300 (2010)). Thus, the WldS mouse provides a genetic test of whether augmented NAD biosynthesis can be used to interfere with axonal degeneration processes.

To test whether augmented NAD biosynthesis protects from noise-induced hearing loss, auditory brainstem responses (ABR) elicited by tone burst stimuli after acoustic trauma was measured. An ABR occurs when a mouse hears the tone burst stimulus. In these experiments, acoustic trauma was elicited in mice by a 90 dB octave band noise exposure for 120 min. To quantify the degree of hearing loss, "threshold shifts" were measured. These shifts refer to the increased level of sound intensity that is required to elicit an ABR. The threshold for detecting sound stimuli is determined by exposing mice to 0.5 msec tone bursts at a specific frequency and volume. The minimum sound intensity which evokes an ABR that shows an increased magnitude with increasing sound intensity is designated the sound threshold for the tested frequency (Willott et al.). Transient threshold shifts (TTS) refer to a temporary hearing loss 24 hours after noise exposure, and permanent threshold shifts (PTS) refer to hearing loss that remains 2 weeks after exposure.

Figure 3A:
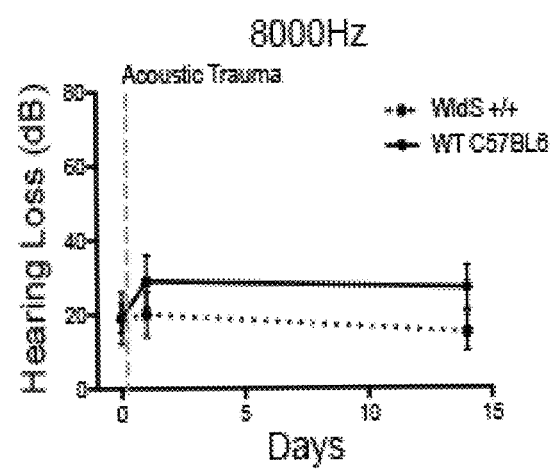
FIGS. 3A-3C depict threshold shifts in noise-exposed WldS mice and wild-type mice that were measured using 8000 Hz, 16,000 Hz and 32,000 Hz tone bursts, respectively.
Figure 3B:
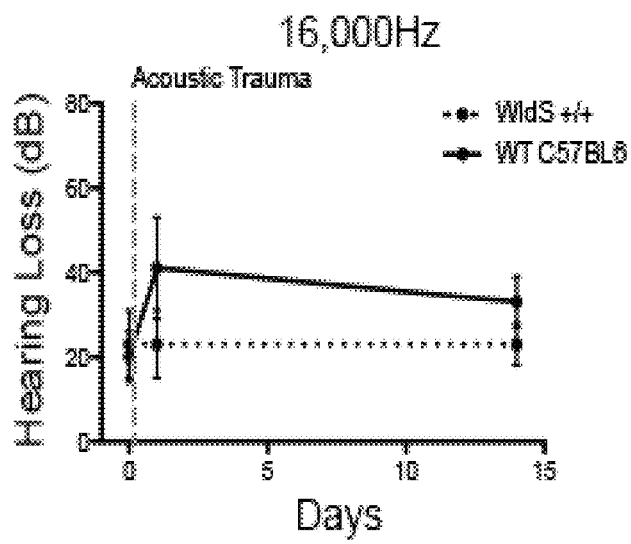
Figure 3C:
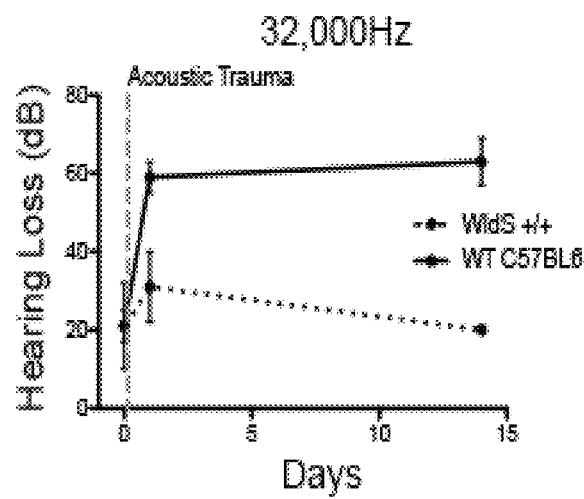

Next, threshold shifts in noise-exposed WldS mice were measured using 8000 Hz, 16,000 Hz and 32,000 Hz tone bursts. In wild-type mice, the transient threshold shift at 32,000 Hz was 38 dB (FIG. 3C). At 16,000 Hz, a threshold shift of 21 dB was observed (FIG. 3B). A smaller shift of 10 dB was noted at 8000 Hz (FIG. 3A). These threshold shifts persisted at 14 days. The persistence of these threshold shifts indicates that the mice have permanent hearing loss. The more prominent hearing loss at higher frequencies following noise exposure is consistent with previous findings (Wang, Y. et al., *Journal of the Association for Research in Otolaryngology,* 3, 248-268 (2002)).

In contrast, the WldS mice exhibited pronounced protection from noise-induced hearing loss. At 24 hours following acoustic trauma, mice exhibited no threshold shift at 8000 and 16,000 Hz, and a mild 10 dB threshold shift at 32,000 Hz (FIGS. 3A-3C). By 14 days, no threshold shift was seen at any frequency. Taken together, these data show that WldS animals exhibit marked resistance to both transient and permanent losses of hearing following acoustic trauma.

Example 3

This example demonstrates that a pharmacologic route for increasing NAD+ levels using nicotinamide riboside as active agent results in protection from hearing loss.

Figure 4A:
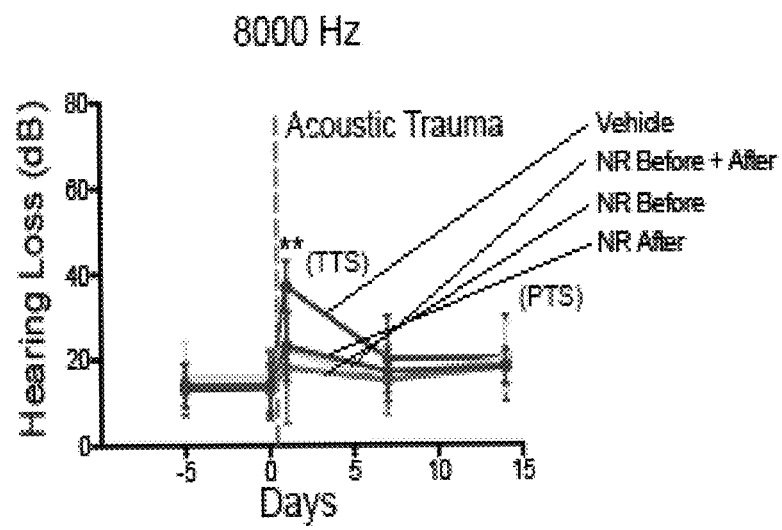
FIGS. 4A-4C depict hearing loss in C57BL6 mice that were either untreated control mice or mice treated with nicotinamide riboside before, after, and both before and after exposure to 8000 Hz, 16,000 Hz and 32,000 Hz tone bursts, respectively.
Figure 4B:
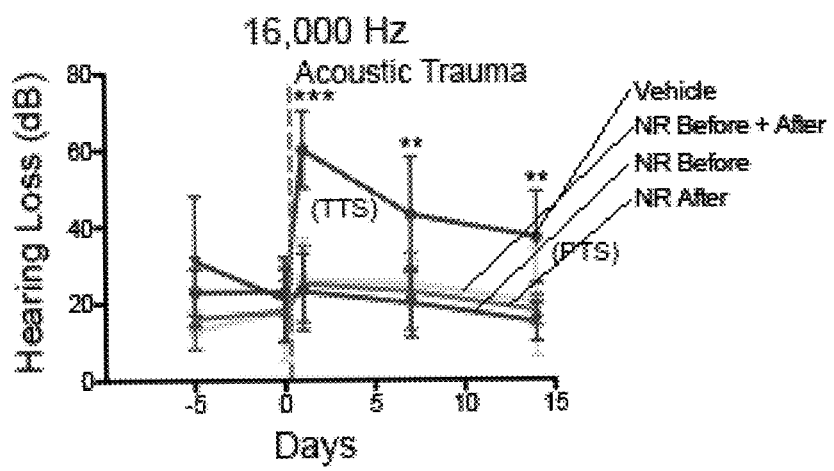
Figure 4C:
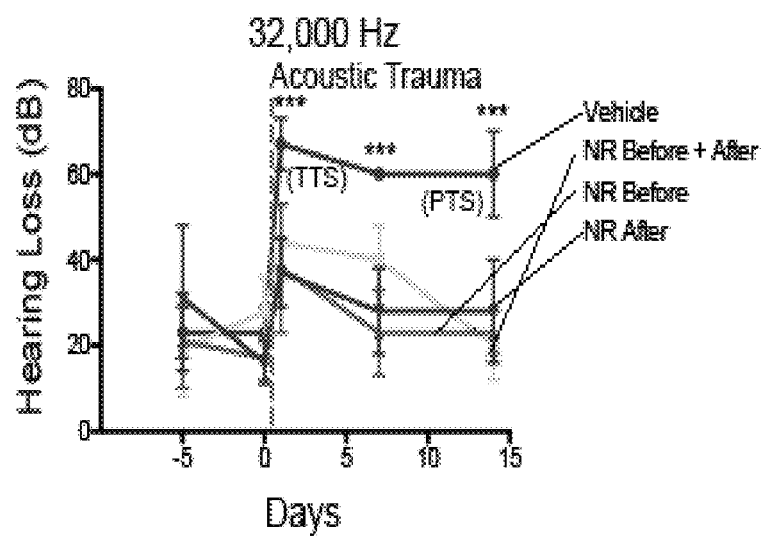

Nicotinamide riboside (NR) is a well-tolerated precursor of NAD+. In these experiments, NR was administered by intraperitoneal injection twice daily at 1000 mg/kg, a dose which increases tissue NAD levels by 50%, either for 5 days prior to noise exposure and 14 days after noise exposure (NR Before+ After), 5 days prior to noise exposure (NR Before), or 14 days after noise exposure (NR After). Compared to vehicle-treated mice, NR-treated mice exhibited negligible transient threshold shifts at 24 hours at 8000 Hz and 16,000 Hz (6 and 8 dB respectively), and a reduced threshold shift at 32,000 Hz (16 dB). The hearing loss at 8000 Hz, 6,000 Hz, and 32,000 Hz is set forth in the Table and is depicted graphically in FIGS. 4A-4C, respectively. Mice were similarly protected from permanent hearing loss at all 3 frequencies. These data indicate that NR treatment markedly reduces noise-induced hearing loss.

TABLE

| Group | | Baseline | | | Pre-noise | | | 24 h post noise | | | 1 wk post noise | | | 2 wks post noise | | |
|---|---|---|---|---|---|---|---|---|---|---|---|---|---|---|---|---|
| | Frequency (kHz) | 8 | 16 | 32 | 8 | 16 | 32 | 8 | 16 | 32 | 8 | 16 | 32 | 8 | 16 | 32 |
| Vehicle only | Avg. hearing loss | 13 | 23 | 23 | 13 | 23 | 23 | 37 | 60 | 67 | 20 | 43 | 60 | 20 | 37 | 60 |
| | St. D | 6 | 6 | 6 | 6 | 6 | 6 | 6 | 10 | 6 | 10 | 15 | 0 | 10 | 12 | 10 |
| NR before and after | Avg. hearing loss | 16 | 13 | 19 | 16 | 18 | 28 | 22 | 26 | 44 | 15 | 25 | 40 | 20 | 20 | 20 |
| | St. D | 8 | | 11 | 5 | 13 | 8 | 8 | 11 | 9 | 6 | 6 | 8 | 8 | 14 | 8 |
| NR before | Avg. hearing loss | 14 | 16 | 21 | 13 | 18 | 17 | 18 | 25 | 38 | 15 | 23 | 23 | 18 | 18 | 23 |
| | St. D | 5 | 8 | 11 | 5 | 8 | 5 | 13 | 10 | 15 | 8 | 10 | 10 | 4 | 4 | 5 |
| NR after | Avg. hearing loss | 14 | 19 | 31 | 14 | 21 | 16 | 23 | 23 | 37 | 17 | 220 | 28 | 18 | 15 | 28 |
| | St. D | 5 | 4 | 17 | 8 | 11 | 5 | 8 | 10 | 8 | 5 | 9 | 10 | 4 | 5 | 12 |

Example 4

This example demonstrates the effect of nicotinamide riboside on retraction of spiral ganglia neurites from the inner hair cells.

Noise-induced hearing loss is associated with retraction of spiral ganglia neurites from the inner hair cells. As the most prominent hearing losses are seen in the portion of the auditory spectrum that contains the highest audible frequencies, the basal turn of the cochlea where this portion of the auditory spectrum is detected was focused on. In this part of the cochlea, noise-induced cellular damage is greatest. Immunofluorescence labeling of the cochlea can readily show whether spiral ganglia neurites are forming their proper contacts with the base of inner hair cells. The base of the inner hair cells is demarcated by the location of the nucleus in these cells, since it rests on the base of the cell. In animals not exposed to noise, spiral ganglia neurites are seen adjacent to the base of the inner hair cells. As expected, in noise-treated animals the spiral ganglia neurites were refracted from inner hair cells by 29.5±12.9 μm 24 hr following noise exposure. The neurites remained retracted (23±3.6 μm) 14 d after noise exposure. The persistent retraction indicates a permanent loss of synaptic connectivity between hair cells and spiral ganglia neurites in vehicle-treated animals after noise exposure.

Figure 5:
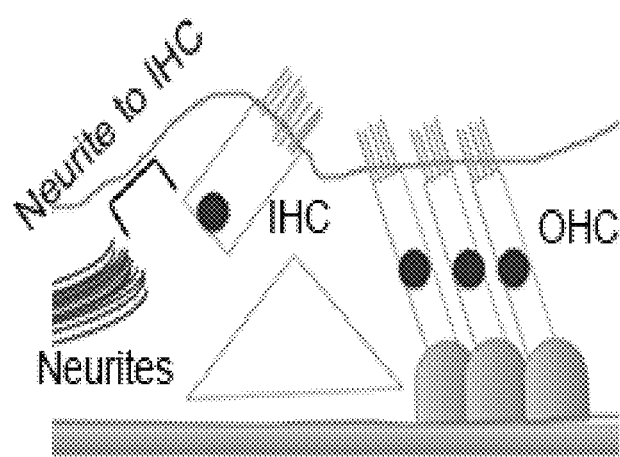
FIG. 5 is a diagrammatic representation of the spatial relation of spiral ganglia neurites to the base of inner hair cells.
Figure 6:
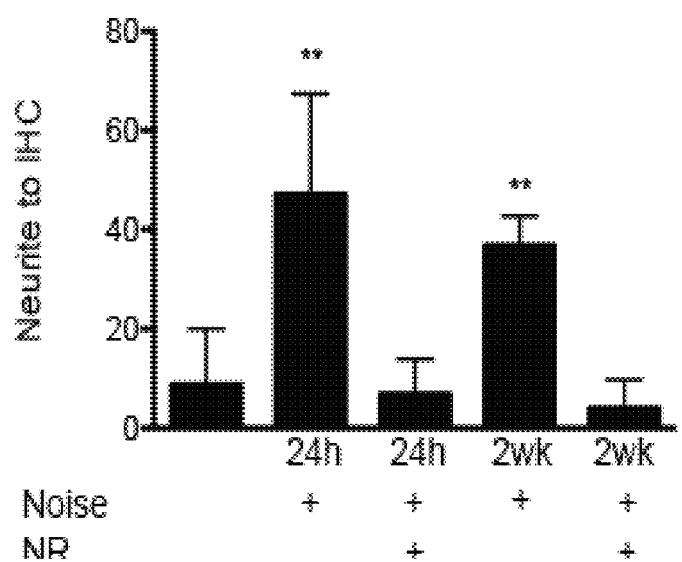
FIG. 6 is a graphical comparison of the distance between spiral ganglia neurites and inner hair cells between noise-exposed mice that were either vehicle-treated control mice or nicotinamide riboside-treated mice at 24 h and 2 weeks after exposure.

Next, spiral ganglia neurites in NR-treated animals were examined. Noise exposure in NR-treated animals resulted in minimal neurite refraction after both 24 hr (4.3±4.5 µm) and 14 d (2.5±3.5 µm). The relationship of spiral ganglia neurites to inner hair cells is shown diagrammatically in FIG. 5. The distances between spiral ganglia neurites and inner hair cells after exposure to noise in control animals and animals treated with NR are illustrated graphically in FIG. 6. Taken together, these data indicate that continuous administration of NR before and after acoustic trauma prevents hearing loss and neurite retraction following noise exposure.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of mitigating or treating hearing loss in a mammal in need thereof, comprising administering to the mammal an effective amount of nicotinamide riboside, thereby mitigating or treating hearing loss in the mammal, wherein the hearing loss is due to noise exposure, and wherein the nicotinamide riboside is administered to the mammal before or during exposure to the noise that causes hearing loss.

2. The method of claim 1, wherein the nicotinamide riboside increases intracellular NAD+ in one or more cells selected from the group consisting of spiral ganglia nerve cells, inner and outer hair cells, supporting cells, and Schwann cells.

3. The method of claim 2, wherein the nicotinamide riboside suppresses oxidative damage in the cell.

4. The method of claim 3, wherein the nicotinamide riboside activates SIRT3.

5. The method of claim 1, wherein the method results in mitigation of hearing loss.

6. The method of claim 1, wherein the nicotinamide riboside is administered orally.

7. The method of claim 1, wherein the mammal is a human or a dog.

8. The method of claim 1, wherein nicotinamide riboside is administered by injection.

9. The method of claim 1, wherein nicotinamide riboside is administered by intratympanic injection into the middle ear space.

* * * * *